(12) United States Patent
Farri et al.

(10) Patent No.: US 11,544,587 B2
(45) Date of Patent: Jan. 3, 2023

(54) PATIENT-CENTRIC CLINICAL KNOWLEDGE DISCOVERY SYSTEM

(71) Applicant: KONINKLIJKE PHILIPS N.V., Eindhoven (NL)

(72) Inventors: Oladimeji Feyisetan Farri, Yorktown Heights, NY (US); Sheikh Al Hasan, Cambridge, MA (US); Junyi Liu, Windham, NH (US); Kathy Mi Young Lee, Westford, MA (US); Vivek Varma Datla, Ashland, MA (US)

(73) Assignee: Koninklijke Philips N.V., Eindhoven (NL)

( * ) Notice: Subject to any disclaimer, the term of this patent is extended or adjusted under 35 U.S.C. 154(b) by 936 days.

(21) Appl. No.: 16/340,480

(22) PCT Filed: Sep. 25, 2017

(86) PCT No.: PCT/EP2017/074155
§ 371 (c)(1),
(2) Date: Apr. 9, 2019

(87) PCT Pub. No.: WO2018/069026
PCT Pub. Date: Apr. 19, 2018

(65) Prior Publication Data
US 2019/0244119 A1    Aug. 8, 2019

Related U.S. Application Data

(60) Provisional application No. 62/406,427, filed on Oct. 11, 2016.

(51) Int. Cl.
*G16H 50/20*    (2018.01)
*G06N 5/04*    (2006.01)
(Continued)

(52) U.S. Cl.
CPC ............ *G06N 5/04* (2013.01); *G06F 16/35* (2019.01); *G06N 3/08* (2013.01); *G16H 15/00* (2018.01);
(Continued)

(58) Field of Classification Search
CPC ....................................... G06F 16/951
See application file for complete search history.

(56) References Cited

U.S. PATENT DOCUMENTS 7,469,251 B2 * 12/2008 Li .................. G06F 40/103
707/999.005
8,166,109 B2 *  4/2012 Lee ................ G10L 15/22
434/350

(Continued)

OTHER PUBLICATIONS

PadmaPriya, et al., "An Approach for Text Summarization Using Deep Learning Algorithm", Journal of Computer Science 10, 2014, pp. 1-9.

(Continued)

*Primary Examiner* — Di Xiao

(57) ABSTRACT

A medical information retrieval system comprises a natural language processing system that processes a vocal user query to identify key words and phrases. These key words and phrases are provided to an inferencing engine that provides a set of knowledge-based inferences from medical knowledge sources, based on these key words and phrases. Thereafter, these knowledge-based inferences are provided to an information retrieval engine that retrieves a corresponding plurality of medical articles based on these knowledge-based inferences, and ranks each with respect to the knowledge-based inferences. A summary engine receives the ranked articles and creates a model based on the topical keywords and candidate sentences found in the highly ranked articles. A paraphrase engine processes the candidate sentences to provide a summary response based on a knowl- (Continued)

edge-based paraphrase model. An audio output device renders the summary report as the response to the user's original vocal query.

12 Claims, 5 Drawing Sheets

(51) Int. Cl.
    *G06F 16/35* (2019.01)
    *G16H 50/70* (2018.01)
    *G16H 15/00* (2018.01)
    *G06N 3/08* (2006.01)
    *G06F 40/30* (2020.01)

(52) U.S. Cl.
    CPC ............. *G16H 50/20* (2018.01); *G16H 50/70* (2018.01); *G06F 40/30* (2020.01)

(56) References Cited

U.S. PATENT DOCUMENTS

| | | |
|---|---|---|
| 2003/0204492 A1 | 10/2003 | Wolf et al. |
| 2009/0037398 A1 | 2/2009 | Horvitz et al. |
| 2010/0174544 A1 | 7/2010 | Heifets |
| 2014/0164401 A1* | 6/2014 | Kyaw ................ G06F 16/9535 707/751 |
| 2015/0006558 A1 | 1/2015 | Leighton et al. |
| 2015/0121200 A1* | 4/2015 | Hamada ................ G06F 16/345 715/243 |
| 2015/0356174 A1* | 12/2015 | Narayana ................ G06F 16/35 707/738 |
| 2016/0147971 A1* | 5/2016 | Kolowitz .............. G06F 3/0482 715/753 |
| 2017/0199963 A1* | 7/2017 | Kondadadi ............ G16H 15/00 |

OTHER PUBLICATIONS

Yao, et al., "Automatic Document Summarization via Deep Neural Networks", 2015 8th International Symposium on Computational Intelligence and Design, pp. 291-296.
Cheng, et al., "Neural Summarization by Extracting Sentences and Words", 10 pages (Abstract).
Cho, et al., "Learning Phrase Representations using RNN Encoder-Decoder for Statistical Machine Translation", 14 pages (Abstract).
Singh, et al., "Bilingual Automatic Text Summarization Using Unsupervised Deep Learning", International Conference on Electrical, Electronics, and Optimization Techniques (ICEEOT) 2016, pp. 1195-1200.
Jolly, et al., "Text Summarization using Neural Network Theory", International Journal of Computer Systems, vol. 3, Issue 7, Jul. 2016, pp. 535-541.
International Search and Written Opinion for International Application No. PCT/EP2017/074155, dated Dec. 15, 2017, 24 pages.
Bhaskar, et al., "From Literature to Knowledge: Exploiting PubMed to Answer Biomedical Questions in Natural Language", ITBAM 2015, LNCS 9267, 2015, pp. 3-15.
Liu, et al., "Query-Oriented Multi-Document Summarization via Unsupervised Deep Learning", Proceedings of the Twenty-Sixth AAAI Conference on Artificial Intelligence, pp. 1699-1705.

* cited by examiner

PATIENT-CENTRIC CLINICAL KNOWLEDGE DISCOVERY SYSTEM

CROSS-REFERENCE TO PRIOR APPLICATIONS

This application is the U.S. National Phase application under 35 U.S.C. § 371 of International Application No. PCT/EP2017/074155, filed on Sep. 25, 2017, which claims the benefit of U.S. Provisional Application Ser. No. 62/406,427, filed Oct. 11, 2016. These applications are hereby incorporated by reference herein, for all purposes.

FIELD OF THE INVENTION

This invention relates to the field of computer enhancements to facilitate efficient and effective retrieval and consolidation of information contained in a patient's medical records, and in particular to a knowledge based discovery system that uses a combination of deep learning, natural language processing, and voice services to process a user's query regarding the information contained in a patient's medical record.

BACKGROUND OF THE INVENTION

Routine processes available on computer systems are not well suited for responding to queries of a non-clinical expert regarding the information contained in records that are designed and implemented for clinical experts, such as queries from a patient regarding the 'meaning' or 'impact' of the information contained in the patient's medical records.

Often, a patient may visit a practitioner to receive the results of a given test or series of tests. The test results may be highly technical, and the practitioner provides a 'translation' of this technical data (hemoglobin count, lipid count, systolic pressure, etc.) into terms that the patient is likely to understand. At the time of this visit with the practitioner, the patient may ask questions and may depart with at least a basic understanding of his/her condition.

In many cases, however, the patient may subsequently realize that he/she doesn't have a complete understanding of his/her condition and thinks of questions that he/she should have asked the practitioner, or thinks of questions to ask of another professional that may serve to validate or contradict the practitioner's diagnoses.

Using conventional computer search techniques, the patient may use a search engine to search for particular terms that the practitioner used, or go to a reference site, such as Wikipedia, to receive an explanation of particular terms or conditions. The results of such searches or references, however, will typically be 'spotty', and provide a less-than-satisfying explanation, because it will be based on the patient's presentation of the particular terms to be searched, and the results may be in a language (medical jargon) that the patient doesn't truly understand.

In essence, due to the patient's non-expert comprehension of the highly technical terms and phrases used in the medical profession, the patient is often limited in his/her ability to formulate a query that reflects the patient's concern while at the same time is sufficient to effect an efficient and effective search through material that is published by professionals in the field. Similarly, even if the patient's query is sufficient to locate applicable references in the field, the mere presentation of the located reference material may be virtually unintelligible to the patient, or the volume of located reference material may simply be too overwhelming for the patient to assimilate in any reasonable amount of time.

Given the current drive for patients' and consumers' access to adequate evidence and relevant information to facilitate well-informed health-related decision-making, there is a need for enhancing existing computer search and reporting tools to process and relay the vast amount of computer-accessible health information to the often 'curious and/or anxious' patient seeking answers to his/her medical dilemmas.

In addition to providing meaningful information to non-clinical experts by aggregating and summarizing the massive amount of facts and findings in existing large volumes of biomedical literature, there is a need to address the fact that patients and consumers may also experience difficulties tailoring their search by using the appropriate technical language to provide efficient retrieval of evidence typically documented in the literature. Enhancing the capabilities of a computer networking system to provide support for patients and consumers to enable construction of efficient and effective queries and provide appropriate answers can significantly improve patient engagement towards motivating adherence to preventative and therapeutic interventions, health awareness and literacy, lifestyle modifications and healthy living.

SUMMARY OF THE INVENTION

It would be advantageous to provide a system and method that substantially improves a computer system's capabilities in the field of medical information retrieval and reporting. Within this framework, it would be advantageous to substantially improve the system's capabilities by facilitating an efficient and effective search based on a user's non-expert query. Also within this framework, it would be advantageous to substantially improve the system's capabilities by facilitating an efficient and effective aggregation and summarization of the retrieved information for the non-expert user.

To better address one or more of these concerns, in an embodiment of this invention, a clinical knowledge discovery system is provided that combines natural language processing (NLP) and deep learning algorithms to retrieve and summarize findings from biomedical publications as answers to queries from patients and other non-expert users. Both audio and textual inputs and outputs may be provided.

In an example embodiment, the medical information retrieval system comprises an input device that receives a user query and a natural language processing system that processes the user query to identify key words and phrases. However, as contrast to conventional search techniques, these key words and phrases are not submitted directly to an information retrieval (search) engine. Instead, these key words and phrases are provided to an inferencing engine that provides a set of knowledge-based inferences from medical knowledge sources based on these key words and phrases.

Thereafter, these knowledge-based inferences are provided to an information retrieval engine that retrieves a corresponding plurality of search results based on these knowledge-based inferences, and ranks each search result with respect to the knowledge-based inferences. A summary engine receives the plurality of ranked search results, identifies topical keywords and candidate sentences based on the plurality of search results, creates a model based on the topical keywords and candidate sentences, and provides a summary report based on the model. An output device renders the summary report as the response to the user's original query.

BRIEF DESCRIPTION OF THE DRAWINGS

The invention is explained in further detail, and by way of example, with reference to the accompanying drawings wherein.

Throughout the drawings, the same reference numerals indicate similar or corresponding features or functions. The drawings are included for illustrative purposes and are not intended to limit the scope of the invention.

DETAILED DESCRIPTION

In the following description, for purposes of explanation rather than limitation, specific details are set forth such as the particular architecture, interfaces, techniques, etc., in order to provide a thorough understanding of the concepts of the invention. However, it will be apparent to those skilled in the art that the present invention may be practiced in other embodiments, which depart from these specific details. In like manner, the text of this description is directed to the example embodiments as illustrated in the Figures, and is not intended to limit the claimed invention beyond the limits expressly included in the claims. For purposes of simplicity and clarity, detailed descriptions of well-known devices, circuits, and methods are omitted so as not to obscure the description of the present invention with unnecessary detail.

Figure 1:
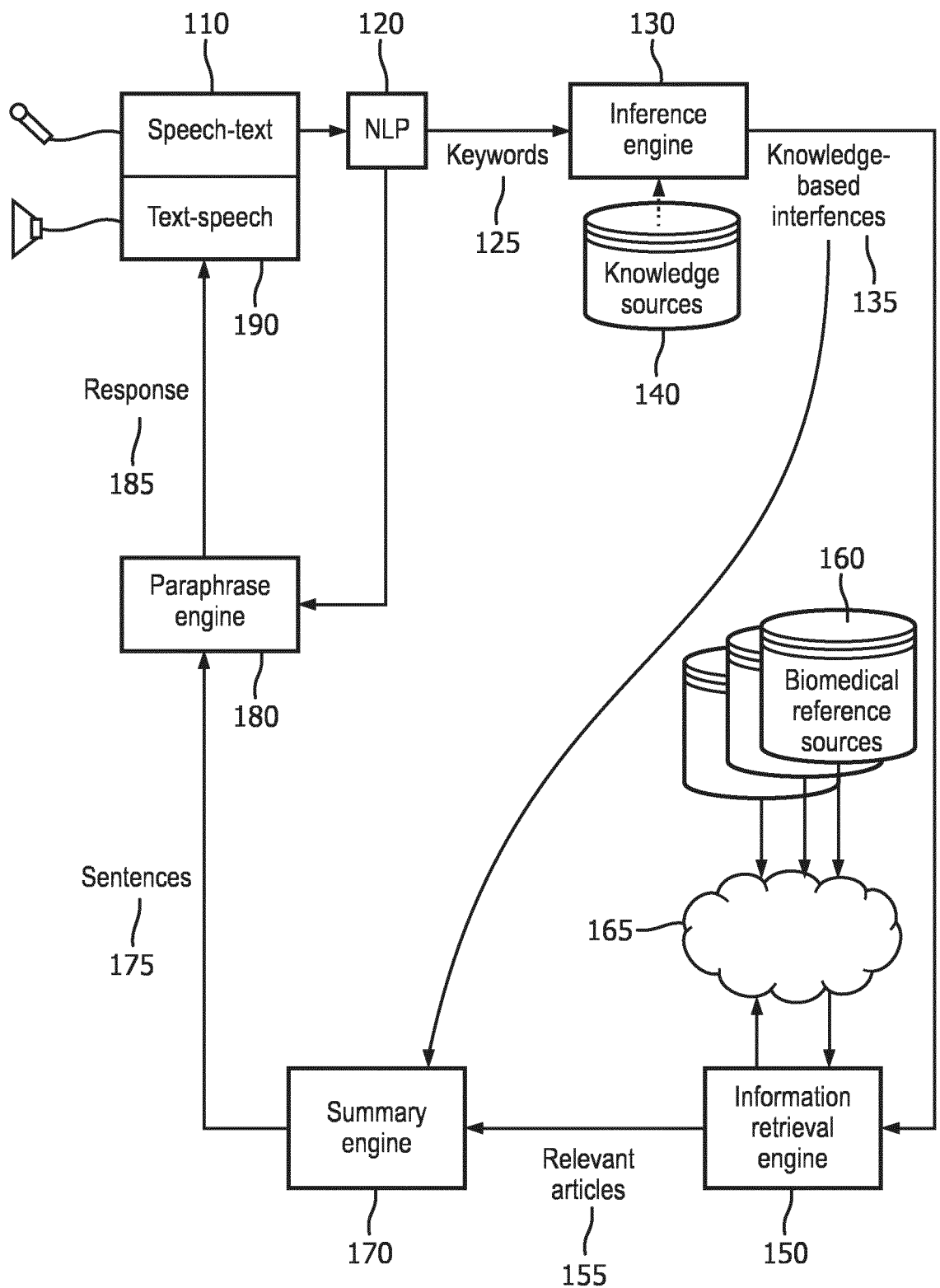
FIG. 1 illustrates an example block diagram of a medical information retrieval system that includes a natural language processor, an inference engine, a search engine, and a summary engine.

FIG. 1 illustrates an example block diagram of an embodiment of a medical information retrieval system in accordance with principles of this invention. In this example embodiment, the system receives queries in the form of spoken statements and/or questions. A speech-to-text converter 110 converts the spoken words and phrases into text using, for example, a conventional speech recognition system.

A natural language processing (NLP) engine 120 analyzes the text from the speech recognition system to identify key words or phrases 125. The NLP engine 120 may be a component of the speech recognition system, and may be specifically designed for the particular context in which it will be used, such as a medical context, to recognize terms that have particular meaning within that context.

In an example embodiment, the NLP engine 120 may include a generic rule-based algorithm for sentence boundary detection; a language model for part-of-speech tagging; and a machine learning classifier trained on the particular language corpus to identify noun phrases, adjective phrases, verb phrases, and so on. A dictionary-driven or ontology-driven process may be used to map the phrases into recognized keywords, and to disambiguate the sense of an extracted word using the contextual elements of the document and/or the application.

The inventors have recognized that a deficiency of searching based on keywords that are extracted from a user's query is that the search terms are substantially limited by the user's vocabulary. Conventional solutions to this deficiency include, for example, ontology-based processes that find alternative terms that are synonymous with the terms provided by the user. However, if the user does not use a term that is synonymous with a particular term, that term will not be included in the search query.

In the example embodiment of FIG. 1, an inference engine 130 within the retrieval system is used to generate "inferences" 135 based on the keywords and phrases 125 derived by the NLP engine 120. The inference engine 130 may be created using an unsupervised machine learning process that is trained using one or more domain-specific knowledge sources 140, as illustrated in FIG. 2.

Figure 2:
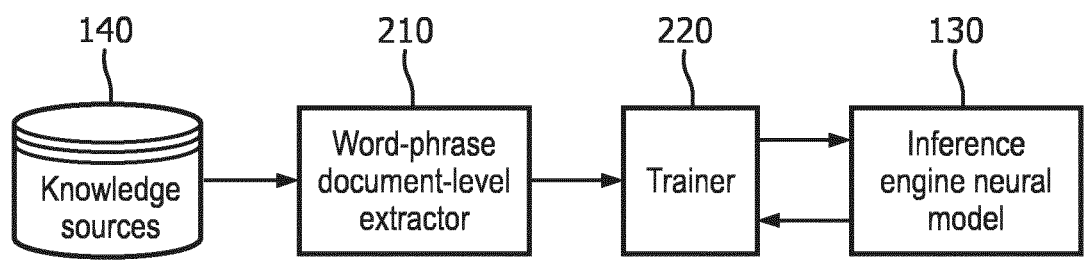
FIG. 2 illustrates an example block diagram for creating an inference engine based on a knowledge source.

In FIG. 2, the knowledge source 140, such as a collection of medical texts, is parsed by an extractor 210. The extractor 210 is configured to extract word-level, phrase-level, and document-level terms that are provided to a trainer 220 coupled to the inference engine 130. The inference engine 130 may be, for example, a neural-network model. Using conventional unsupervised learning techniques, the inference engine 130 may be trained to recognize the relationships among the medical terms and phrases contained in the knowledge source 140. For example, using word-level, phrase-level and document-level vector representations of a large number of sentences from the knowledge source 140, distributed clusters may be generated from aggregated contributions of these vector representations ('neural embeddings').

After training, when a word or phrase is subsequently provided to the inference engine 130, the inference engine 130 will provide the medical terms or phrases that are most closely related to that word or phrase. In an example embodiment, the distributed clusters may be ranked based on semantic relevance. The top ranked clusters may be further parsed to retrieve knowledge-based inferences; that is, the inferences are synonymous to the subjects of documents from the knowledge sources in which the most keywords are represented.

Figure 3:
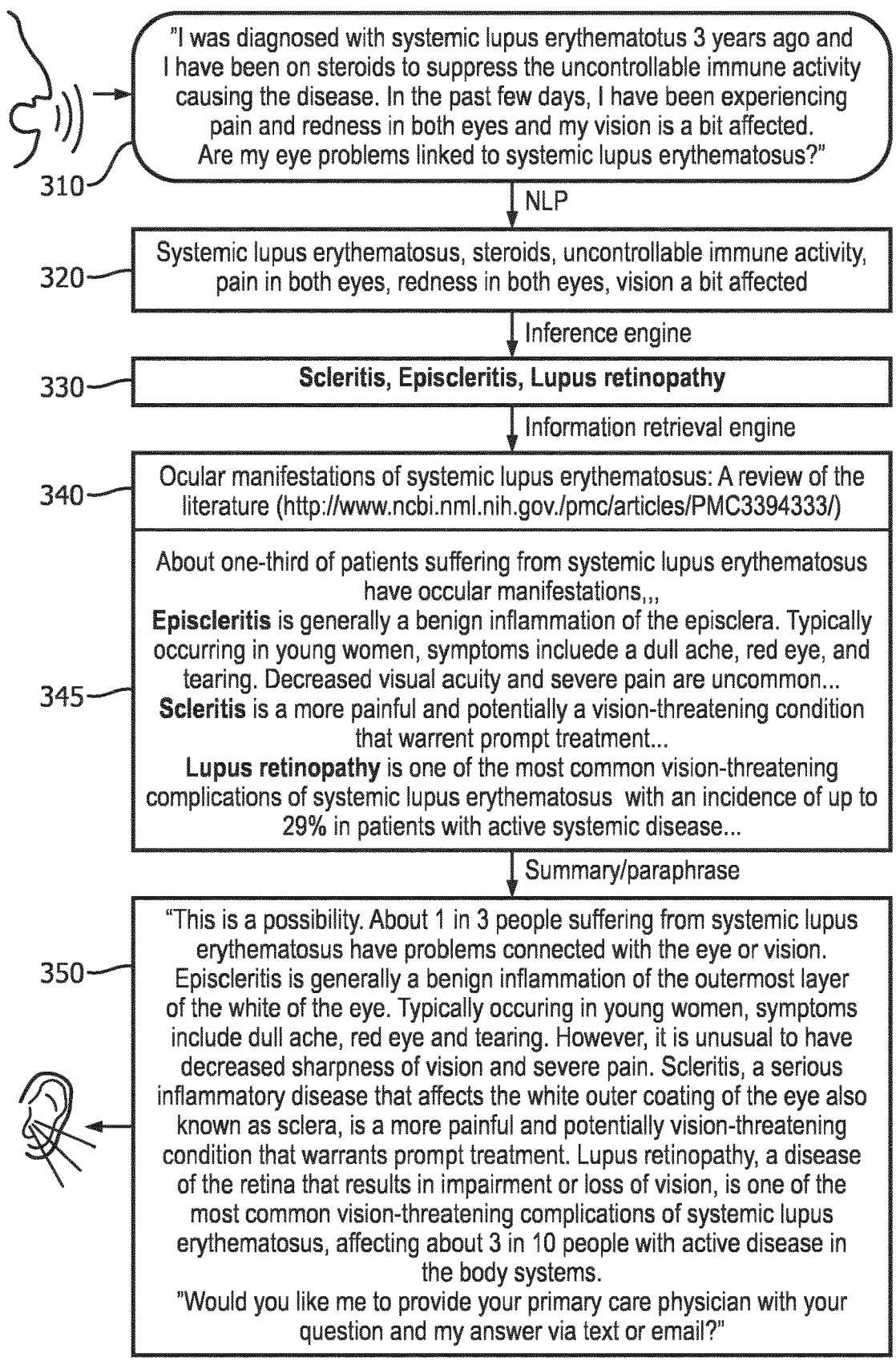
FIG. 3 illustrates an example user query and a response provided by the medical information retrieval system.

FIG. 3 provides an example processing of a user's query. At 310, a user provides a spoken question regarding whether recent eye problems are related to the user's systemic lupus erythematosus. After speech-to-text conversion and natural language processing, a set of keywords 320 are identified. In this example, the natural language processing engine includes recognition of medical terms, such as 'systemic lupus erythematosus'. Of particular note, each of the identified keywords 320 are terms that are contained in the user's spoken query 310. As noted above, the keyword extraction process may be configured to identify synonyms that may be considered more encompassing, or more precise, than the particular terms in the user's query. However, the presence of such synonyms in the keywords is still dependent upon the presence of the particular term in the user's query.

In the medical information retrieval system of this disclosure, the computer system's ability to find pertinent information related to the user's query is significantly enhanced by a pre-search enhancement of the user's query to generate search terms that are more consistent with a 'professional' medical vocabulary. That is, for example, the enhanced search terms may be similar to the terms that a medical student (or diagnostician) might submit to a search engine if the medical student had a similar question regarding the potential relationship between eye problems and systemic lupus erythematosus.

In the example of FIG. 3, the keywords 320 that were extracted from the user's query 310 are provided to the aforementioned medical-knowledge-based inference engine (130 of FIGS. 1 and 2). The inference engine processes the user's keywords to produce a set of "knowledge-based inferences" 330. In this example, the inferences provided are "scleritis," "episcleritis", and "lupus retinopathy". Of particular note, other than the word "lupus", these inferences do not appear in the user's query. The inference engine received the keywords related to eye problems and produced corresponding medical terms "scleritis", and "episcleritis" (inflammation of the sclera and episclera, corresponding to pain and redness in both eyes), and "lupus retinopathy" (lupus-related vision problem, corresponding to vision a bit affected). As noted above, a medical student might automatically use the terms scleritis and episcleritis instead of "pain and redness of the eyes" when researching eye symptoms, and may be aware of retinopathy related to lupus.

With regard to FIG. 2, the inference engine 130 received keywords related to pain and redness of the eyes, and determined a correspondence with the terms scleritis and episcleritis based on its learning from the medical knowledge source 140. That it, it is likely that the knowledge source's entries regarding scleritis and episcleritis contained phrases such as eye pain or redness, and the inference engine 130 established a strong neural link between eye pain and redness with scleritis and episcleritis, so that when "redness in both eyes" and "pain in both eyes" were provided to the inference engine, the inference engine's 'inference' was "scleritis" and "episcleritis". A similar strong neural link in the inference engine 130 was also likely established between "systemic lupus erythematosus", "affected vision", and "lupus retinopathy", based on the content of the knowledge source 140 related to lupus retinopathy.

By converting the user-provided keywords "systemic lupus erythematosus", "steroids", "uncontrollable immune activity", "pain in both eyes", "redness in both eyes", "vision a bit affected" 320 into the more professional terms "scleritis," "episcleritis", and "lupus retinopathy" 330, the information retrieval system's ability to find reference material that addresses the user's query can be expected to be substantially improved, because the searched reference material (published medical articles and the like) is more likely to contain the terms "scleritis" and "episcleritis" than they are to contain "redness in both eyes" or "pain in both eyes".

One of skill in the art will recognize that the user-provided keywords may also be included in the knowledge-based inferences, to potentially also search for articles written for non-professionals, such as articles prepared by support organizations for patients with particular diseases.

Returning to FIG. 1, the knowledge-based inferences 135 are provided to an Information Retrieval (IR) engine 150 that searches biomedical reference sources 160 for relevant articles 155. In one embodiment, the IR engine 150 may be specifically configured to search for medical terms among medical reference sources 160, although one of skill in the art will recognize that in some embodiments, the IR engine 150 may be a commonly used search engine, such as 'Google', 'Bing', 'Yahoo', and so on.

Although the reference sources 160 may include the references used as the knowledge source 140, it is expected that the reference sources 160 will be far more extensive than the knowledge source 140. That is, the knowledge source 140 will generally be one or more medical texts from which it is feasible to create an inference engine 130, whereas it would be impractical/infeasible to attempt to access and analyze all of the medical reference sources 160 that are potentially available world-wide, in "the cloud" 165 via the Internet. Conversely, to provide information that is likely to be most relevant to the user's query, it is unlikely that the knowledge source 140 would include the depth of information required, and a search of the substantially larger set of all available medical reference sources 160 would likely be more effective.

The IR engine 150 preferably ranks and filters the results of the search of the reference sources 160 based on the correspondence between the knowledge-based inferences and terms in the title and abstract of the articles; in the species and particular demographics reflected in the articles; in meta-data associated with the articles; and so on. The date of publication may also be analyzed by the IR engine 150 to ensure that the information provided to the user is current and/or to give recent publications more weight than older publications.

As noted above, because the knowledge-based inferences 135 will generally provide terms that are commonly used by professionals in the medical field, the likelihood of identifying an appropriately relevant article within the myriad of biomedical reference sources 160 is substantially improved.

In the example of FIG. 3, the IR engine identifies an article 340 on "Ocular Manifestations of Systemic Lupus Erythematosus" as a highly relevant article that addresses the user query. Within the article 340, the contents 345 include each of the knowledge-based inferences 330, an explanation of each, and their relationships with systemic lupus erythematosus (the inferences are illustrated in bold in FIG. 3, for ease of understanding; they are not bold in the article 340).

As indicated by the ellipses ( . . . ) in the contents 345, the relevant article 340 includes much more information than illustrated, and likely much more information, and more detailed information than the user would want as an answer to the user's query 310. As illustrated in FIG. 1, a summary engine 170, and a paraphrase engine 180 are used to condense and restructure the available information 345, to provide a response 185 that is suitable for the user.

Returning to FIG. 1, the relevant articles 155 from the information retrieval engine 150 are processed by a Summary engine 170.

Figure 4:
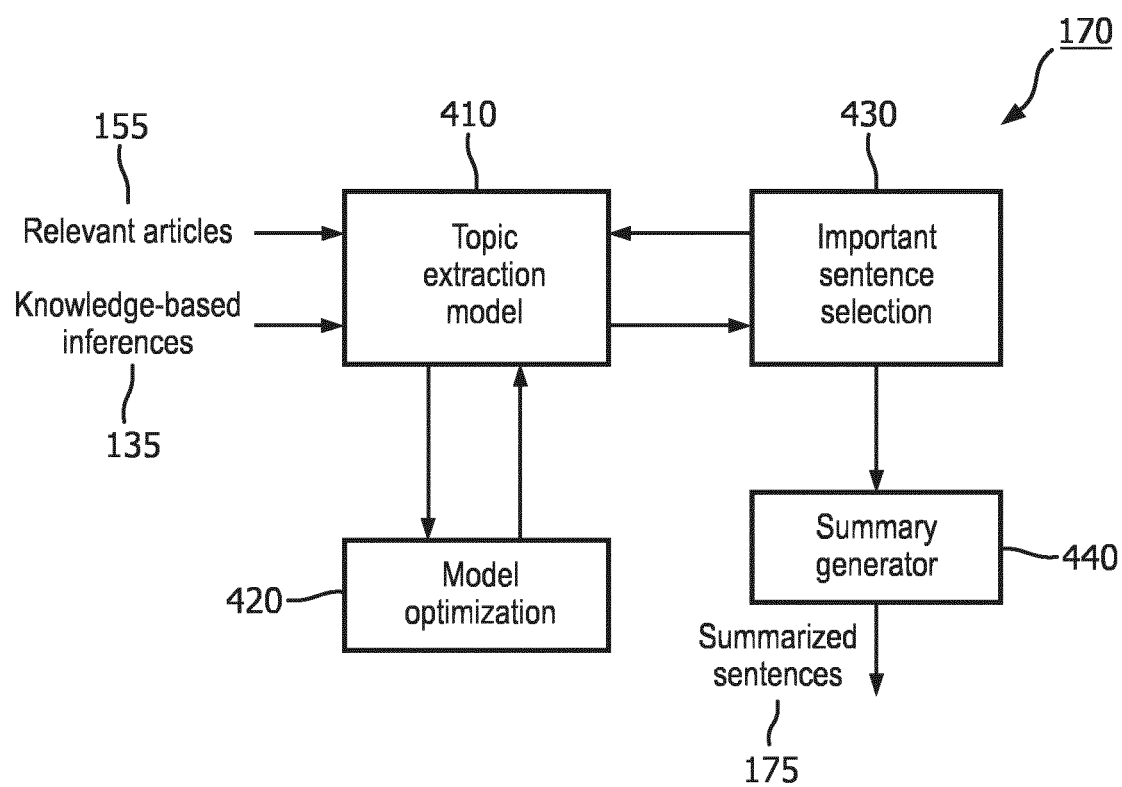
FIG. 4 illustrates an example block diagram of a summary engine.

FIG. 4 illustrates an example block diagram of an embodiment of a Summary engine 170. In this example embodiment, an unsupervised deep learning architecture for document summarization is implemented based on a Restricted Boltzmann Machine (RBM)-based framework. The example RBM of FIG. 4 includes a topic extraction model 410 that includes a neural network architecture that uses symmetrically weighted connections between input (results 135 from the inferencing engine 130, and documents/biomedical articles 155 retrieved by the IR engine 150 based on the keywords and phrases representing the results 135) and outputs (relevant sentences contained in the retrieved articles 155).

This model is optimized 420 using top-down and bottom-up optimization techniques, also known as forward and back propagation techniques. Top-down connections are used to learn abstract feature representations, such as semantic properties of the sentences in the articles 155, from low-level feature vectors that represent properties of the words/terms in the sentences. For example, Term Frequency-Inverse Document Frequency (TF-IDF) may be used to assess the significance of a term in a sentence compared to the overall presence of the term in the article.

Bottom-up connections are exploited to validate the effectiveness of the learned representations. In particular, multiple hidden layers are used to sequentially learn about important topical keywords and important candidate sentences from the retrieved articles towards building a model that is globally optimized via the backpropagation algorithm by tuning the model parameters in a bottom-up fashion.

In the example of FIG. 3, if the inferencing engine gives "scleritis, episcleritis and lupus retinopathy" as results 330 (135 in FIGS. 1 and 4) and the IR engine in turn gives the article "Ocular Manifestations of SLE: A Review of the Literature" as a relevant article 340 (155 in FIGS. 1 and 4) because it contains the aforementioned inferences 330 in the abstract and/or body of the article, the summary engine 170 would then process as input all the sentences in the article 340 with mentions of the knowledge-based inferences 330 and learn the semantic properties of these sentences enough for the model 410 to decipher if several sentences share the same meaning and can be combined into a single sentence.

The important sentence selection module 430 selects sentences from the model 410 that are deemed to have the most significance with respect to the knowledge-based inferences 135. These sentences are provided to a summary generator 440 to provide the set of summarized sentences 175. The summary generator 440 may be configured to limit the number of words in the summarized sentences 175, to provide a concise answer to the original narrative/question.

The summarized sentences 175 from relevant articles are further simplified by using the paraphrase engine 180 to provide a more user-friendly response 185 to the original query.

Figure 5:
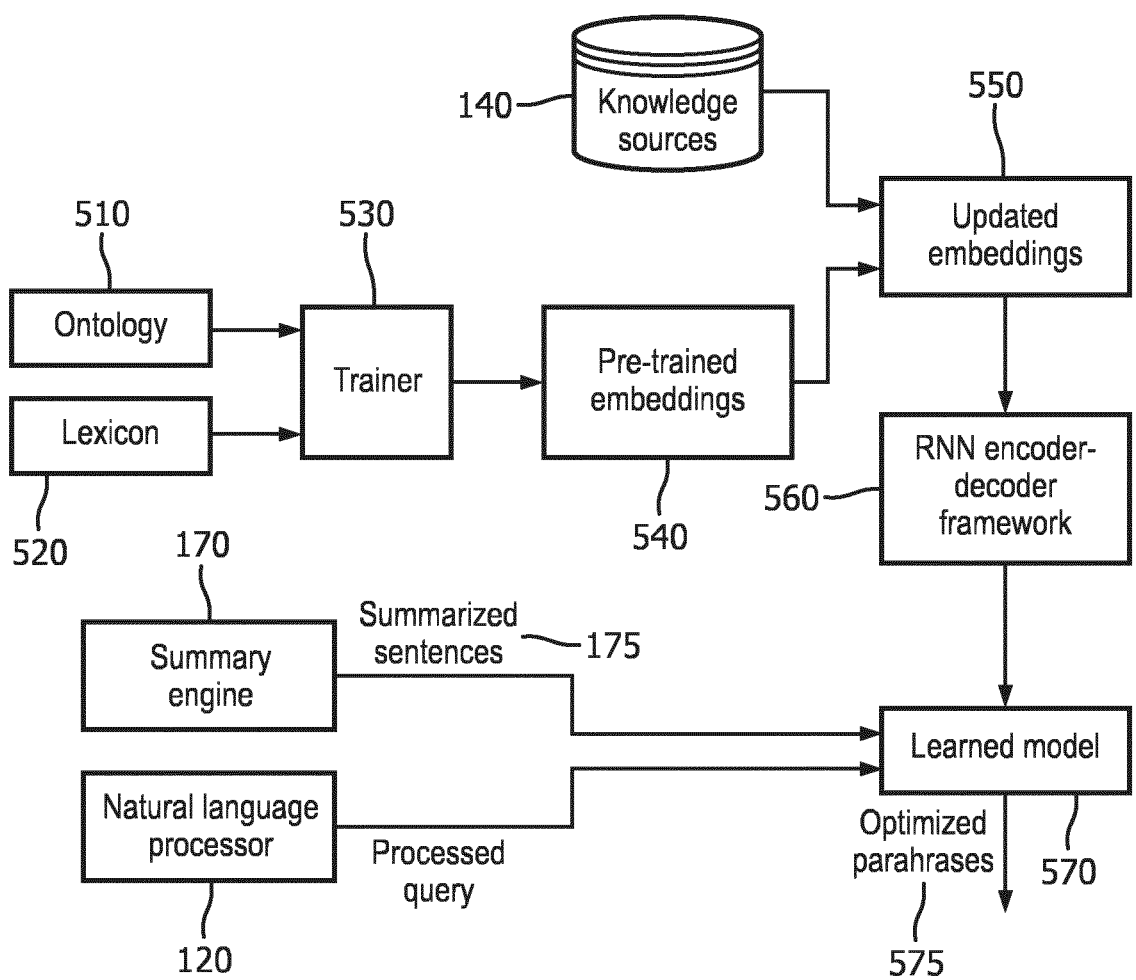
FIG. 5 illustrates an example block diagram of a paraphrase engine.

FIG. 5 illustrates an example block diagram of a paraphrase engine. In this embodiment, a large amount of parallel clinical domain data is extracted from open-source biomedical ontologies 510, such as Medical Subject headers (MeSH)), along with an aligned collection of general English Lexicon 520, to construct the training data for a trainer 530 of the paraphrasing engine. The trainer 530 uses the training data 510, 520 to learn pre-trained word/phrase embeddings 540, which are further refined using the available clinical knowledge sources 140, to create updated embeddings 550.

A Recurrent Neural Network (RNN)-based encoder-decoder framework 560 may be used to build a model 570 from these updated embeddings 550. The resulting model 570 is exploited to generate optimal paraphrases 575 (185 of FIG. 1) from the summarized sentences 175 from the summary engine 170 in order to simplify the response, and appear as a 'natural' response to the original query provided by the natural language processor 120, as illustrated in the example response 350 of FIG. 3.

Returning to FIG. 1, the response 185, comprising the summarized and paraphrased sentences, is transformed to an audio output by the text-speech converter 190 to provide audible and easily comprehensible response to the initial vocal user query. question (narrative) the patient/consumer vocalized. Overall, this disclosure supports the discovery of relevant clinical evidence from biomedical literature that may otherwise be very difficult to comprehend by clinically-naïve patients/consumers, facilitating optimal user experience as individuals search and find accurate answers to medical dilemmas when needed.

While the invention has been illustrated and described in detail in the drawings and foregoing description, such illustration and description are to be considered illustrative or exemplary and not restrictive; the invention is not limited to the disclosed embodiments.

For example, alternative embodiments can be used to customize the response for a particular class of users. The summary 170 and paraphrasing 180 engines, for example, may be configured to reduce or minimize the presence of 'uncommon' medical terms in the paraphrased response 185, such as the knowledge-based inferences 135 that may be provided by the inference engine 130, to enable easier readability for a more 'casual' enquirer. In like manner, the summary 170 and paraphrasing 180 engines may be configured to also accept the keywords 125 that the user provided in the original query as additional inputs for optimizing the models 410, 570 within these engines. Similarly, the information retrieval engine 150 may be configured to use both the knowledge-based inferences 135 and the user's keywords 125 in the search of the biomedical reference sources 160.

The elements of the disclosure may be suitably embodied by one or more configured processors, such as one or more Intel® Core™ or Pentium™ processors of a computing device such as Lenovo ThinkCenter, Dell Inspiron, HP Envy, and so on. The configured processor(s) executes computer readable instructions stored in computer readable storage medium of the aforementioned computing device, such as the Intel® SSD 600p. The computing device also includes network adapters, such as an Intel® Ethernet Connection and corresponding software that enable the device to communicate with other sources of information via a local area network or a wide area network, such as the Internet. The computing device also includes peripheral devices, including input devices such as a keyboard, mouse, touchpad, microphone, camera, and the like for receiving input from a user, and output devices such display screens, speakers, printers, and the like for providing output to the user. The computing device can comprise a workstation, laptop, tablet, smart phone, server, and the like. The lines between components represented in the figures represent communications paths, which can be wired or wireless.

In an embodiment, the configured computer device interacts with a user to process a user query using natural language processes to identify key words and phrases. The computer readable instructions enable the processor to be configured as an inferencing engine that processes the key words and phrases and provides a plurality of knowledge-based inferences from one or more local or remote medical knowledge sources, and provides the plurality of knowledge-based inferences to an information retrieval engine, such Microsoft's Explorer web-browser that searches one or more biomedical reference sources to identify a plurality of computer-readable medical articles based on the plurality of knowledge-based inferences. The configured processor ranks each article with respect to the knowledge-based inferences to identify one or more target articles, then summarizes the one or more target articles by identifying topical keywords and candidate sentences in the target articles. Using the topical keywords and candidate sentences, the configured processor creates a summary report, and provides the summary report to an output device that renders the summary report in response to the user query.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The invention claimed is:

1. A medical information retrieval system comprising:
an input device that receives a user query;
a natural language processing system that processes the user query to identify key words and phrases;
an inferencing engine that receives the key words and phrases and provides a plurality of knowledge-based inferences from medical knowledge sources based on the key words and phrases;
an information retrieval engine that receives the plurality of knowledge-based inferences and searches a plurality of biomedical reference sources to identify a plurality of medical articles based on the plurality of knowledge-based inferences, and ranks each article with respect to the knowledge-based inferences;
a summary engine that receives the plurality of ranked articles, identifies topical keywords and candidate sentences based on the ranked articles, and provides a summary report based on the topical keywords and candidate sentences;
a paraphrase engine that provides paraphrased sentences based on the candidate sentences to the summary report, wherein the paraphrase engine includes a Recurrent Neural Network based encoder/decoder framework; and
an output device that renders the summary report in response to the user query.

2. The system of claim 1, wherein the input device includes an audio input device, and the output device includes an audio output device.

3. The system of claim 1, wherein the inferencing engine includes a neural model that is trained using the medical knowledge sources, and provides the knowledge-based inferences upon receipt of the key words and phrases.

4. The system of claim 1, wherein the medical knowledge sources include one or more medical texts.

5. The system of claim 1, wherein the plurality of biomedical reference sources are accessed via an Internet connection.

6. The system of claim 1, wherein the summary engine creates a model based on the topical keywords and candidate sentences, and uses the model to create the summary report.

7. The system of claim 1, wherein the summary engine includes a Restricted Boltzmann Machine.

8. A non-transitory computer-readable medium that includes a program that, when executed by a processing system, causes the processing system to:
receive a user query;
processes the user query using natural language processes to identify key words and phrases;
provide the key words and phrases to an inferencing engine that provides a plurality of knowledge-based inferences from medical knowledge sources based on the key words and phrases;
provide the plurality of knowledge-based inferences to an information retrieval engine that searches one or more biomedical reference sources to identify a plurality of medical articles based on the plurality of knowledge-based inferences;
rank each article with respect to the knowledge-based inferences to identify one or more target articles;
summarize the one or more target articles by identifying topical keywords and candidate sentences in the target articles;
provide the candidate sentences to a paraphrase engine that provides paraphrased sentences based on the candidate sentences, wherein the paraphrase engine includes a Recurrent Neural Network based encoder/decoder framework;
create a summary report based on the topical keywords and paraphrased sentences; and
provide the summary report to an output device that renders the summary report in response to the user query.

9. The medium of claim 8, wherein the processing system receives the user query and provides the summary report in audible form.

10. The medium of claim 8, wherein the inferencing engine includes a neural model that is trained using the medical knowledge sources, and provides the knowledge-based inferences upon receipt of the key words and phrases.

11. The medium of claim 8, wherein the medical knowledge sources include one or more medical texts, and the information retrieval engine accesses the plurality of biomedical reference sources via an Internet connection.

12. The medium of claim 8, wherein the summary engine includes a Restricted Boltzmann Machine.

* * * * *